United States Patent [19]

Whisson

[11] Patent Number: 5,728,073
[45] Date of Patent: Mar. 17, 1998

[54] SYRINGE

[75] Inventor: Maxwell Edmund Whisson, Perth, Australia

[73] Assignee: Eastland Technology Australia Pty Ltd., Wangara, Australia

[21] Appl. No.: 809,590

[22] PCT Filed: Oct. 4, 1995

[86] PCT No.: PCT/AU95/00650

§ 371 Date: Mar. 26, 1997

§ 102(e) Date: Mar. 26, 1997

[87] PCT Pub. No.: WO96/10433

PCT Pub. Date: Apr. 11, 1996

[30] Foreign Application Priority Data

Oct. 4, 1994 [AU] Australia ............... PM 8598

[51] Int. Cl.⁶ ............................................. A61M 5/00
[52] U.S. Cl. .................. 604/194; 604/195; 604/220
[58] Field of Search .............................. 604/194, 195, 604/110, 187, 198, 263, 218, 220

[56] References Cited

U.S. PATENT DOCUMENTS

| 5,263,942 | 11/1993 | Smedley et al. | 604/195 |
| 5,300,038 | 4/1994 | Haber et al. | 604/187 |
| 5,498,245 | 3/1996 | Whisson | 604/198 |

FOREIGN PATENT DOCUMENTS

| 26288 | 6/1989 | Australia. |
| 0 479 303 A1 | 4/1995 | European Pat. Off.. |
| 9309824 | 5/1993 | WIPO. |
| 9217230 | 10/1995 | WIPO. |

*Primary Examiner*—John D. Yasko
*Attorney, Agent, or Firm*—Merchant Gould, Smith, Edell, Welter & Schmidt, P.A.

[57] ABSTRACT

A syringe comprising a tubular body (11) closed at one end (12) and open at the other end (13), a plunger (14) receivable in the body (11) to define a chamber (16) of variable volume, a needle support (24) adapted to support and accommodate a hollow needle, said needle support (24) being supported from or in the wall of the body (11) and being movable in a direction substantially parallel to the main axis of the body (11) between a first position at which the needles extends from the one end of the body (11) and the interior of the needle is in communication with the chamber (16), and a second position at which the outer end of the needle is in a retracted position, said needle support (24) having a protrusion (28) which is selectively engageable with the wall of the body (11) at the first and second positions to be able to be retained at said positions and receivable through the wall of the body (11) when at the second position to be engaged with the plunger (14) to prevent axial movement of both the needle support (24) and the plunger (14) with respect to the body (11).

13 Claims, 6 Drawing Sheets

SYRINGE

THIS INVENTION relates to syringes and in particular syringes of the form which incorporate a retractable needle.

As a result of the need to develop practices which minimise the risk of infection the use of disposable syringes has become commonplace. The principal difficulty of such syringes however relates to the need to prevent the spread of infection as a result of inadvertent "stick" injuries. These can result from accidents during the use of the syringes and the inappropriate disposal of the syringe. In many cases these can be avoided if the pointed needle can be stored in a retracted position when not in use and in particular prior to disposal. In addition it is highly desirable to prevent such syringes from being reused. As a result syringes have been proposed in which the needle can be moved between a retracted position and an extended position. Some of these syringes are provided with a locking means which is able to prevent a used syringe from being reused by lockingly retaining the needle of a used syringe in the retracted position to prevent its reuse. Examples of such syringes are disclosed in the following patent specifications: AU-A-17419/92; U.S. Pat. No. 4,927,414; and U.S. Pat. No. 4,941,883.

A difficulty of such syringes however is that the plunger is still capable of being used to draw and force fluid from the chamber of the syringe which means that if the needle can be disengaged from its locking engagement, the syringe can be reused.

It is an object of this invention to provide a syringe whereby when the needle is located in the retracted position in which it is fully accommodated within the syringe body, it can be locked in that position.

Accordingly the invention resides in a syringe comprising a tubular body closed at one end and open at the other end, a plunger receivable in the body to define a chamber of variable volume, a needle support adapted to support and accommodate a hollow needle, said needle support being supported from, or in the wall of the body and being movable in a direction substantially parallel to the main axis of the body between a first position at which the needle extends from the one end of the body and the interior of the needle is in communication with the chamber and a second position at which the outer end of the needle is in a retracted position, said needle support having a protrusion which is selectively engagable with the wall of the body at the first and second positions to be able to be retained at said positions and receivable through the wall of the body at the second position to be engaged with the plunger to prevent axial movement of both the needle support and the plunger with respect to the body.

According to a preferred feature of the invention the needle support is rotatable about an axis substantially parallel to its direction of movement and said protrusion extends radially from the needle support, whereby rotation of the needle support will cause the protrusion to pass through the wall of the body and engage the plunger.

According to a further preferred feature of the invention the needle support is receivable in a passage provided on or in the wall of the body and is slidable along the passage to enable movement between the first an second position. The passageway can be formed with a longitudinal slot which slidably receives the protrusion. If desired the slot can be formed with a transverse extension at a position corresponding to the position of the protrusion at both the first and the second position whereby rotation of the needle support will cause the protrusion to engage with respective slot when at the first and second position.

According to a further preferred feature an aperture is provided in the wall adjacent the transverse slot at said second position to permit the protrusion to pass through the wall to engage the plunger. The aperture is dimensioned to require resilient deformation of the protrusion and/or the edges of the aperture to permit the passage of the protrusion through the aperture.

According to a further preferred feature the plunger is formed with a radial abutment surface along its length which will engage the protrusion when in the engaged position to prevent said axial movement of the plunger. The abutment surface can be located such that when the plunger is substantially fully received within the body the abutment surface is capable of being engaged by the protrusion. If desired a plurality of abutment surfaces can be provided along the length of the plunger. In one form the abutment surface is provided by a recess in the side of the plunger. In another form the abutment surface is formed by a radial flange provided along the length of the plunger.

The invention will be more fully understood in the light of the following description of several specific embodiments. The description is made with reference to the accompanying drawings of which:

Figure 1:
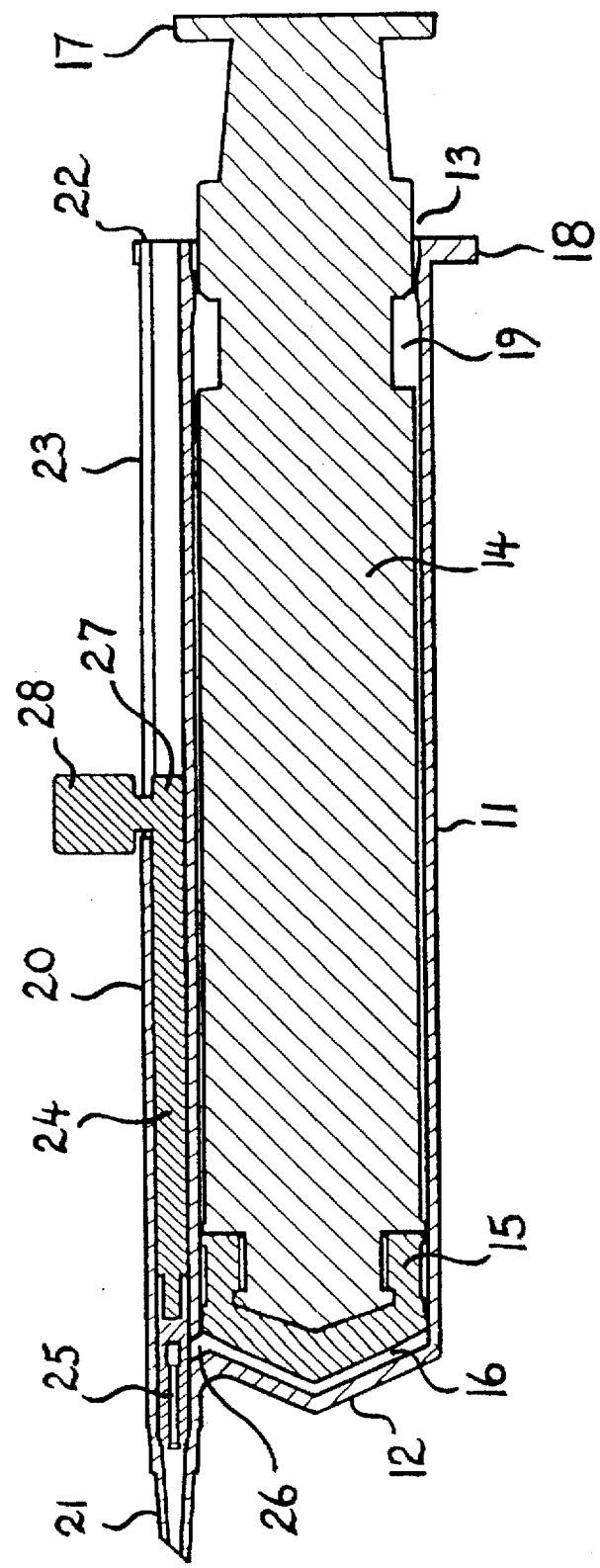
FIG. 1 is a sectional side view of the first embodiment showing the needle support in the extended position.
Figure 2:
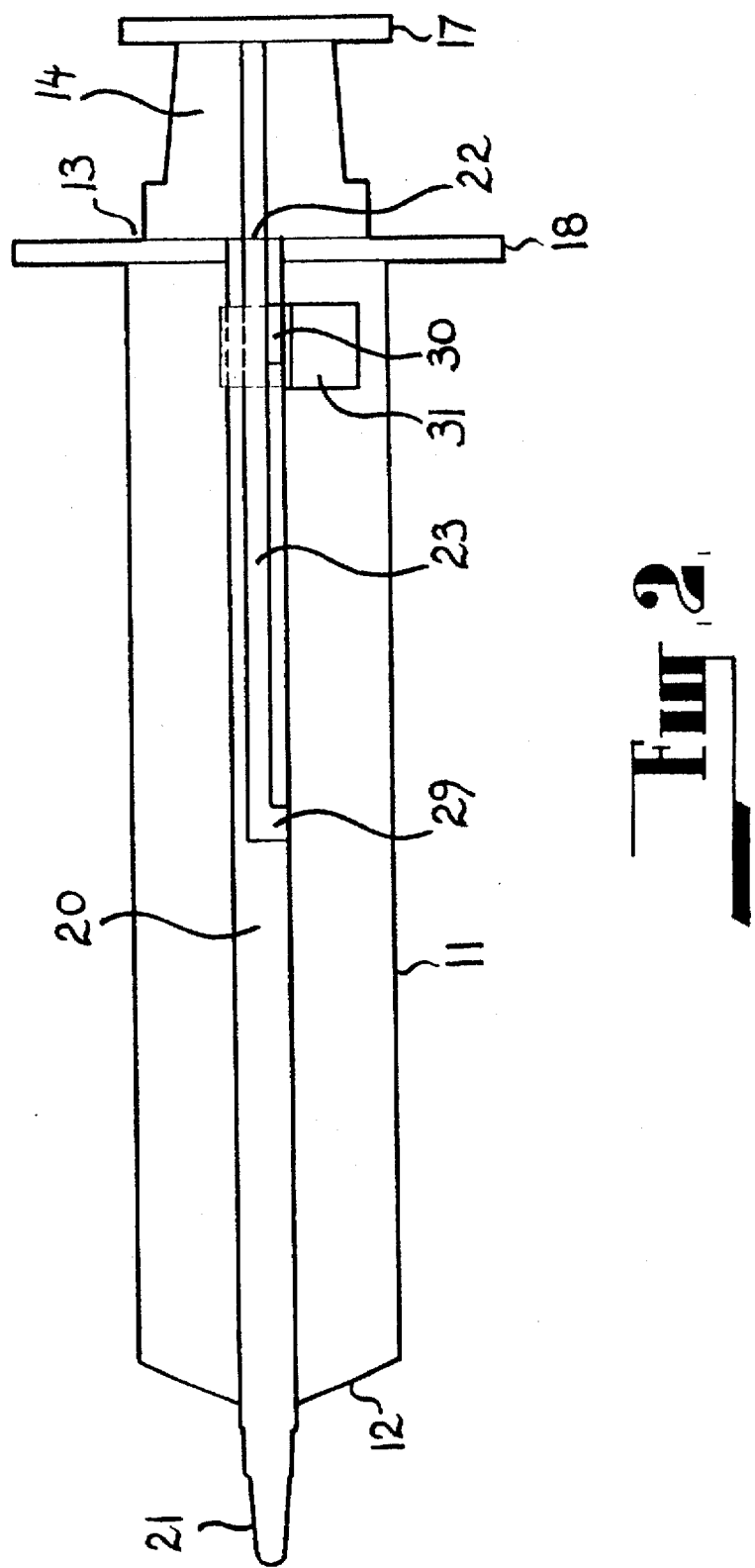
FIG. 2 is a side elevation of the syringe body of the body of the first embodiment without the needle support located therein.
Figure 3:
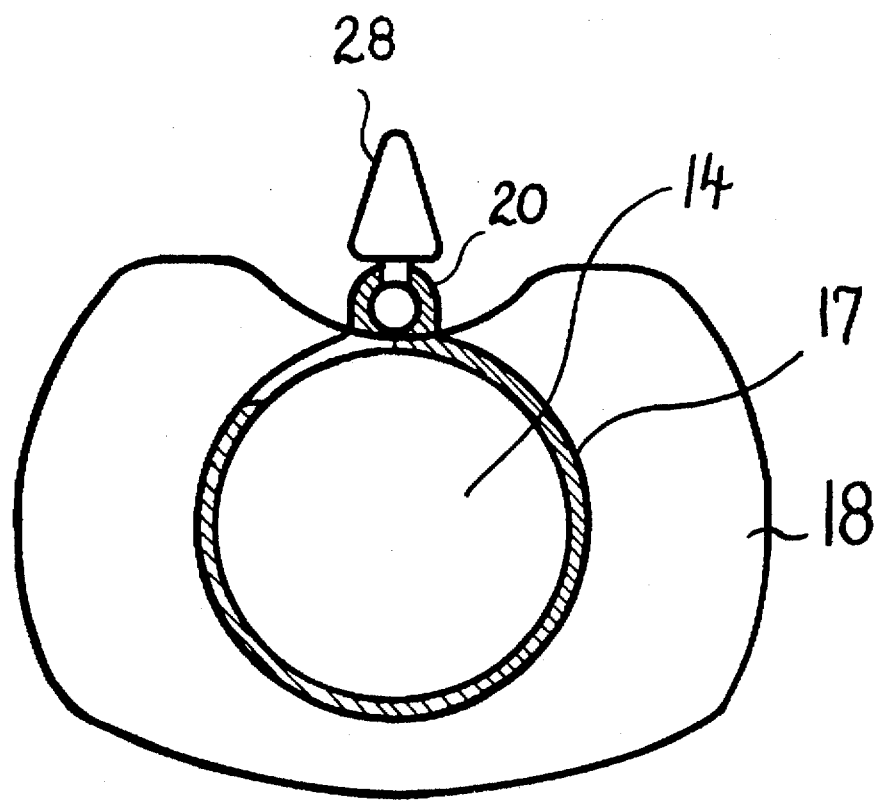
FIG. 3 is an end elevation of the first embodiment as shown at FIG. 1.

The first embodiment as shown in the accompanying drawings comprises a syringe of the general form disclosed in patent specification WO 88/08315. The syringe has a tubular body 11 which is closed at one end 12 and is open at the other end 13. The tubular body supports a plunger 14 which is slidably received within the body and is provided with a seal 15 at its inner end which defines chamber 16 between the inner end of the plunger 14 and the one end 12 of the body and which is of variable volume. The outer end of the plunger 14 is provided with suitable handle 17 or manipulation means to facilitate gripping of the plunger by the operator and the other end 13 of the body is provided with a lateral flange 18 to facilitate manipulation by the operator.

The side of the plunger 14 is formed with a recessed portion 19 which provides a pair of spaced abutment surfaces. The recessed portion is located towards the other end of the plunger and is positioned to be located within the body 11 when the plunger is fully received within the body 11.

The outer wall of the body is formed with a tubular portion 20 which provides a passage which is substantially parallel therewith. One end 21 of the tubular portion 20 which is adjacent the one end 12 of the body 11 is formed as a pointed tubular boss which may be formed to be capable of accommodating a "LUER" or like fitting or alternatively may be pointed or similarly sharpened to be able to pierce a closure provided on a conventional phial or a like container.

The wall of the tubular member 20 between the other end 22 is formed with a longitudinal slot 23.

Figure 4:
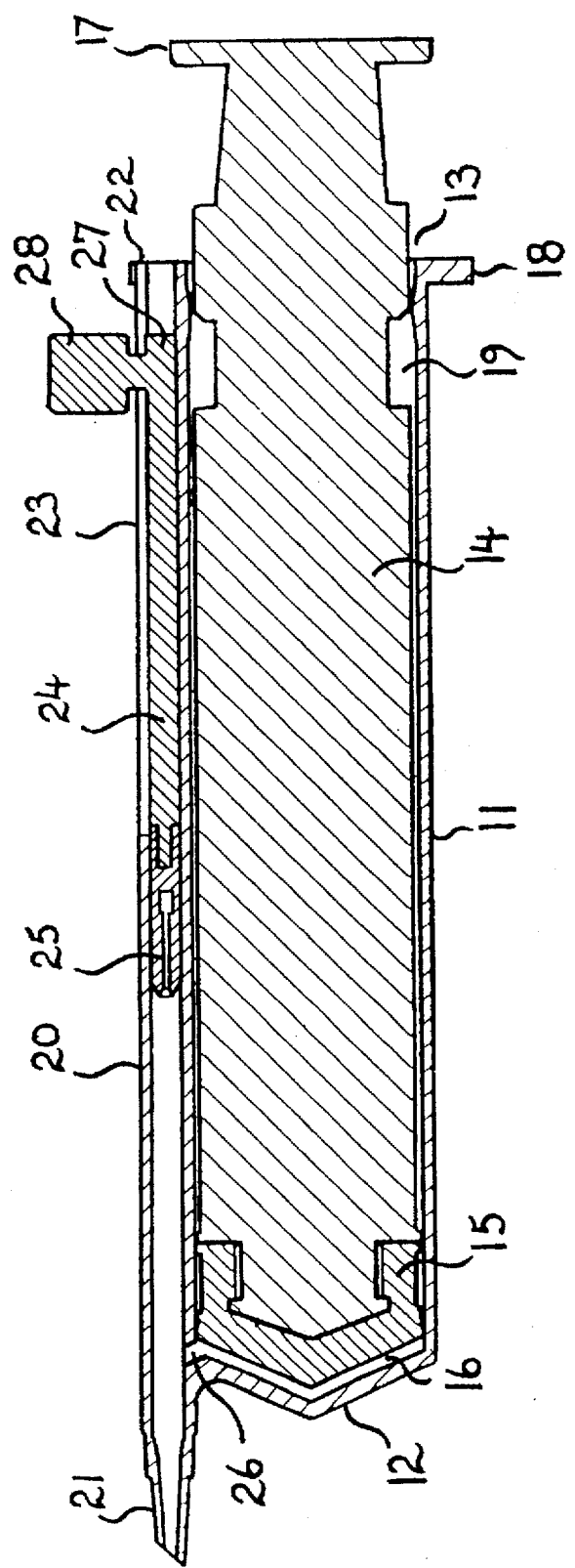
FIG. 4 is a sectional side view of the first embodiment with the needle support in the retracted position.

The tubular member 20 slidably supports a needle support 24 which is slidably received within the tubular member 20 to be movable towards a first position at which its one end 25 is adjacent the one end 21 of the tubular member 20 as shown at FIG. 1 and a second position as shown at FIG. 4 at which the one end 25 is remote from the one end 21 of the tubular member 20. The one end 25 of the needle support 24 is adapted to receive a hollow needle (not shown) which when the needle support is in the extended position as shown at FIG. 1 will extend through the tubular boss 21 to extend from the syringe body.

An opening 26 is provided between the chamber 16 and the interior of the tubular member at one end of the body 11. The end 25 of the needle support 24 is adapted to sealingly engage the side walls of the interior of the tubular member in the region of the opening 26 and provide communication between the opening 26 and the interior of the hollow needle when in the extended position as shown at FIG. 1.

The other end 27 of the needle support is provided with a radial protrusion 28 which is configured to be able to be manipulated to facilitate manual movement of the needle support between the first position as shown at FIG. 1 and the second position as shown at FIG. 4. The longitudinal slot 23 enables the longitudinal movement of the protrusion 28 between those two positions. The innermost end of the longitudinal slot 23 is formed with a transverse extension 29 whereby when the needle support is in the first position as shown at FIG. 1, the needle support can be caused to rotate about its central axis whereby the protrusion 28 is received in the innermost transverse slot 29 and the needle body is retained in the extended first position. A second transverse slot 30 is provided towards the outer end of the longitudinal slot 23 whereby on rotation of the needle support 24 when the protrusion 28 is in the region of the second transverse slot, the protrusion 28 can be moved laterally.

In order to lockingly retain the needle support in the second position and limit the movement of the plunger the wall of the body 11 on the corresponding side of the tubular member 21, and at the location of the second transverse slot 30 is formed with an aperture 31 which is configured to receive the protrusion 28 on rotation of the needle support 24 within the tubular member 20. The location of the transverse slot 30 and aperture 31 corresponds to the position of the recessed portion 19 of the plunger 14 when the plunger is fully accommodated within the tubular body 11.

Figure 5:
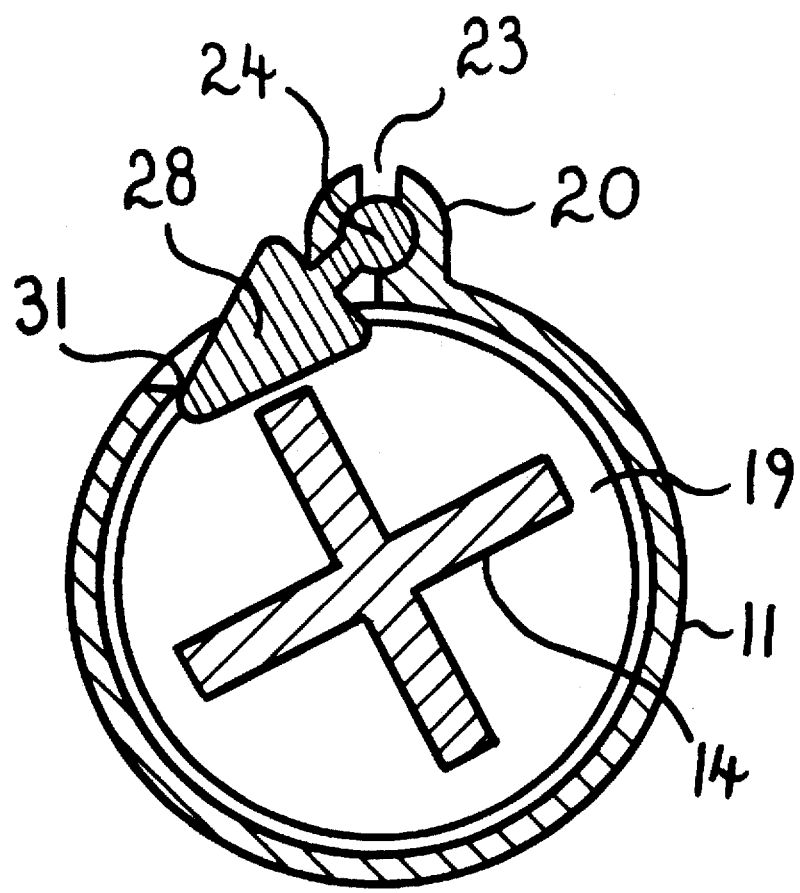
FIG. 5 is a cross section of the embodiment with the needle supported in the retracted position and the protrusion in the locked position.

As shown at FIG. 5, the protrusion is configured such that when the plunger is fully received within the body and the needle support is in its retracted second position the needle support can be caused to rotate about its central axis whereby the protrusion 28 is able to move through the transverse slot 30 and through the aperture 31, to be received within the recessed portion 19 of the plunger 17. The aperture 31 is slightly smaller than the protrusion 28 such that when the protrusion 28 is caused to rotate into engagement with the aperture 31, and is fully engaged therewith such that its outer edge moves past the inner face of the wall of the body of the tubular body, the wall in the region of the aperture and/or the protrusion is caused to undergo some resilient deformation to permit the movement of the protrusion through the wall. As result the protrusion becomes positively engaged within the body and cannot be easily extracted from the body without damaging the body, or the protrusion or the needle support. Once so engaged, the needle is fully accommodated within the tubular member 20, the plunger 14 is fully accommodated within the body 11 and the syringe is unusable since the needle support and plunger have been lockingly and substantially irretrievably engaged with the body 11.

According to an alternative form of the first embodiment the plunger may be formed with a number of recessed portions along the length whereby the syringe can be rendered unusable, even if not empty.

Figure 6:
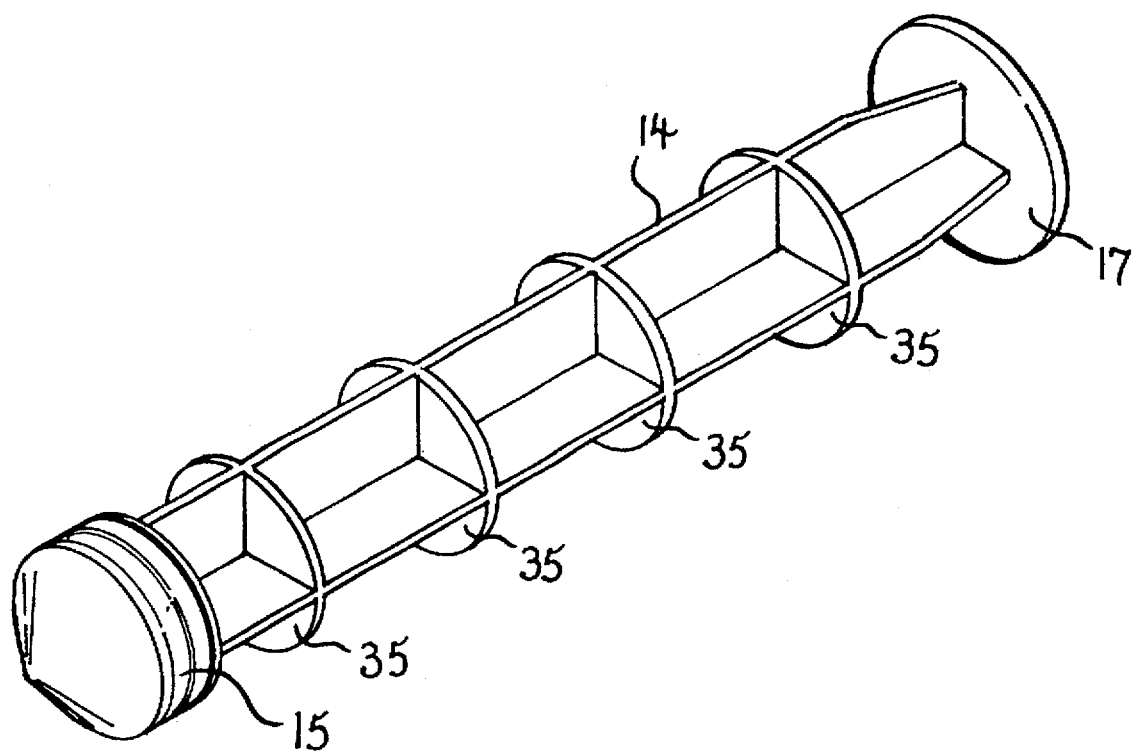
FIG. 6 is an isometric view of a plunger according to a second embodiment of the invention.

According to a second embodiment as shown in FIG. 6 the plunger may be formed with a plurality of radial flanges 35 to provide abutment surfaces. The flanges 35 serve the function of the recessed portion 19 of the first embodiment Once the protrusion 28 is received through the aperture 31 the presence of the flanges will limit the relative movement of the plunger within the body. The number of flanges can be varied as desired.

It should be appreciated that the scope of the present invention need not be limited to the particular scope of the embodiment described above.

I claim:

1. A syringe comprising a tubular body closed at one end and open at the other end, a plunger receivable in the body to define a chamber of variable volume, a needle support adapted to support and accommodate a hollow needle, said needle support being supported from, or in the wall of the body and being movable in a direction substantially parallel to the main axis of the body between a first position at which the needle extends from the one end of the body and the interior of the needle is in communication with the chamber and a second position at which the outer end of the needle is in a retracted position, said needle support having a protrusion which is selectively engagable with the wall of the body at the first and second positions to be able to be retained at said positions and receivable through the wall of the body at the second position to be engaged with the plunger to prevent axial movement of both the needle support and the plunger with respect to the body.

2. A syringe as claimed at claim 1, wherein the needle support is rotatable about an axis substantially parallel to its direction of movement and said protrusion extends radially from the needle support, whereby rotation of the needle support will cause the protrusion to pass through the wall of the body and engage the plunger.

3. A syringe as claimed at claim 1 wherein the needle support is receivable in a passage provided on or in the Wall of the body and is slidable along the passage to enable movement between the first and second position.

4. A syringe as claimed at claim 3 wherein the passageway is formed with a longitudinal slot which slidably receives the protrusion.

5. A syringe as claimed at claim 4 wherein the slot is formed with a transverse extension at a position corresponding to the position of the protrusion at both the first and the second position whereby rotation of the needle support will cause the protrusion to engage with respective slot when at the first and second position.

6. A syringe as claimed at claim 5 wherein an aperture is provided in the wall at a position adjacent the transverse slot at said second position to permit the protrusion to pass through the wall to engage the plunger.

7. A syringe as claimed at claim 6 wherein the aperture is dimensioned to require resilient deformation of the protrusion and/or the edges of the aperture to permit the passage of the protrusion through the wall.

8. A syringe as claimed at claim 1 wherein the plunger is formed with a radial abutment surface along its length which will engage the protrusion when in the engaged position to prevent said axial movement of the plunger.

9. A syringe as claimed at claim 8 wherein the abutment surface is located such that when the plunger is substantially fully received within the body the abutment surface is capable of being engaged by the protrusion.

10. A syringe as claimed at claim 8 wherein a plurality of abutment surfaces provided along the length of the plunger.

11. A syringe as claimed at claim 8 wherein the abutment surface is provided by a recess in the side of the plunger.

12. A syringe as claimed at claim 8 wherein the abutment surface is provided by radial flange provided along the length of the plunger.

13. A syringe as claimed at claim 1 wherein the protrusion comprises a enlargement which is receivable through the wall of the body and is engagable with the plunger.

* * * * *